(12) United States Patent  
Drew et al.

(10) Patent No.: US 8,465,515 B2  
(45) Date of Patent: Jun. 18, 2013

(54) TISSUE RETRACTORS

(75) Inventors: Daniel W. Drew, Loveland, OH (US); Michael D. Cronin, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1208 days.

(21) Appl. No.: 11/846,787

(22) Filed: Aug. 29, 2007

(65) Prior Publication Data

US 2009/0062618 A1   Mar. 5, 2009

(51) Int. Cl.
*A61B 17/00* (2006.01)

(52) U.S. Cl.
USPC .......................................... 606/204; 606/203

(58) Field of Classification Search
USPC .................................. 600/201–246
See application file for complete search history.

(56) References Cited

U.S. PATENT DOCUMENTS

| | | | |
|---|---|---|---|
| 3,522,800 A * | 8/1970 | Lesser ............................ | 600/206 |
| 3,545,008 A * | 12/1970 | Bader, Jr. .................... | 623/13.15 |
| 4,271,828 A * | 6/1981 | Angelchik ...................... | 600/37 |
| RE32,922 E | 5/1989 | Levin et al. | |
| 4,979,956 A * | 12/1990 | Silvestrini .................. | 623/13.11 |
| 4,984,564 A | 1/1991 | Yuen | |
| RE33,585 E | 5/1991 | Haber et al. | |
| 5,062,847 A | 11/1991 | Barnes | |
| 5,152,279 A | 10/1992 | Wilk | |
| 5,163,942 A | 11/1992 | Rydell | |
| 5,178,133 A | 1/1993 | Pena | |
| 5,195,505 A | 3/1993 | Josefsen | |
| 5,195,506 A | 3/1993 | Hulfish | |
| 5,267,554 A | 12/1993 | Wilk | |
| 5,271,385 A | 12/1993 | Bailey | |
| 5,273,026 A | 12/1993 | Wilk | |
| 5,280,782 A | 1/1994 | Wilk | |
| 5,301,658 A | 4/1994 | Zhu et al. | |

(Continued)

FOREIGN PATENT DOCUMENTS

| | | |
|---|---|---|
| EP | 288879 A2 | 11/1988 |
| EP | 353916 A1 | 2/1990 |

(Continued)

OTHER PUBLICATIONS

"Ribbon". Webster's New World College Dictionary, Internet URL :http://www.yourdictionary.com/ribbon, webpage accessed on Feb. 25, 2011.*

(Continued)

*Primary Examiner* — Eduardo Robert
*Assistant Examiner* — Jerry Cumberledge

(57) ABSTRACT

Methods and devices are provided for performing surgical procedures using tissue retractors. In general, the methods and devices allow a surgeon to use a retractor to capture a large or small amount of tissue in a fabric and to move the fabric to relocate the tissue to one or more convenient locations during the procedure. The flexible nature of the fabric can allow the fabric to be moveable between an open position, in which the fabric can support tissue, and a closed position, in which the fabric can be folded, rolled, or otherwise compressed in size and fit through a port, such as a trocar or an incision in a tissue wall. Furthermore, the position of the fabric and thus the tissue held in the fabric can be adjusted and readjusted by pushing or pulling one or more grasping elements coupled to the fabric.

10 Claims, 13 Drawing Sheets

U.S. PATENT DOCUMENTS

| | | | |
|---|---|---|---|
| 5,309,896 A | 5/1994 | Moll et al. | |
| 5,318,586 A | 6/1994 | Ereren | |
| 5,337,736 A | 8/1994 | Reddy | |
| 5,339,801 A | 8/1994 | Poloyko et al. | |
| 5,352,237 A | 10/1994 | Rodak et al. | |
| 5,353,784 A | 10/1994 | Nady-Mohamed | |
| 5,359,995 A | 11/1994 | Sewell, Jr. | |
| 5,361,752 A | 11/1994 | Moll et al. | |
| 5,362,294 A * | 11/1994 | Seitzinger | 600/37 |
| 5,381,788 A | 1/1995 | Matula et al. | |
| 5,391,180 A | 2/1995 | Tovey et al. | |
| 5,400,773 A | 3/1995 | Zhu et al. | |
| 5,402,772 A | 4/1995 | Moll et al. | |
| 5,415,666 A | 5/1995 | Gourlay et al. | |
| 5,425,357 A | 6/1995 | Moll et al. | |
| 5,439,476 A | 8/1995 | Frantzides | |
| 5,441,044 A | 8/1995 | Tovey et al. | |
| 5,450,843 A | 9/1995 | Moll et al. | |
| 5,454,367 A | 10/1995 | Moll et al. | |
| 5,465,711 A | 11/1995 | Moll et al. | |
| 5,468,248 A | 11/1995 | Chin et al. | |
| 5,512,037 A | 4/1996 | Russell et al. | |
| 5,514,075 A | 5/1996 | Moll et al. | |
| 5,514,157 A | 5/1996 | Nicholas et al. | |
| 5,527,264 A | 6/1996 | Moll et al. | |
| RE35,312 E | 8/1996 | Christoudias | |
| 5,549,636 A | 8/1996 | Li | |
| 5,554,101 A | 9/1996 | Matula et al. | |
| 5,562,603 A | 10/1996 | Moll et al. | |
| 5,569,165 A | 10/1996 | Chin et al. | |
| 5,575,759 A | 11/1996 | Moll et al. | |
| 5,582,577 A * | 12/1996 | Lund et al. | 600/204 |
| 5,588,951 A | 12/1996 | Zhu et al. | |
| 5,591,182 A | 1/1997 | Johnson | |
| 5,690,607 A | 11/1997 | Chin et al. | |
| 5,716,327 A | 2/1998 | Warner et al. | |
| 5,722,935 A | 3/1998 | Christian | |
| 5,728,047 A * | 3/1998 | Edoga | 600/227 |
| 5,738,629 A | 4/1998 | Moll et al. | |
| 5,743,851 A | 4/1998 | Moll et al. | |
| 5,755,661 A | 5/1998 | Schwartzman | |
| 5,772,680 A | 6/1998 | Kieturakis et al. | |
| 5,803,902 A | 9/1998 | Sienkiewicz et al. | |
| 5,810,721 A * | 9/1998 | Mueller et al. | 600/206 |
| 5,823,945 A | 10/1998 | Moll et al. | |
| 5,840,011 A * | 11/1998 | Landgrebe et al. | 600/30 |
| 5,860,987 A | 1/1999 | Ratcliff et al. | |
| 5,865,728 A | 2/1999 | Moll et al. | |
| 5,865,802 A | 2/1999 | Yoon et al. | |
| 5,885,271 A | 3/1999 | Hamilton et al. | |
| 5,906,205 A | 5/1999 | Hiebert | |
| 6,010,447 A * | 1/2000 | Kardjian | 600/29 |
| 6,036,640 A | 3/2000 | Corace et al. | |
| 6,042,534 A * | 3/2000 | Gellman et al. | 600/30 |
| 6,056,768 A | 5/2000 | Cates et al. | |
| 6,063,112 A | 5/2000 | Sgro | |
| 6,090,042 A | 7/2000 | Rullo et al. | |
| 6,146,401 A | 11/2000 | Yoon et al. | |
| 6,159,201 A | 12/2000 | Hamilton et al. | |
| 6,162,172 A | 12/2000 | Cosgrove et al. | |
| 6,179,852 B1 | 1/2001 | Strickland et al. | |
| 6,190,311 B1 | 2/2001 | Glines et al. | |
| 6,199,556 B1 | 3/2001 | Benetti et al. | |
| 6,248,062 B1 | 6/2001 | Adler et al. | |
| 6,248,119 B1 | 6/2001 | Solem | |
| 6,264,604 B1 * | 7/2001 | Kieturakis et al. | 600/207 |
| 6,309,349 B1 | 10/2001 | Bertolero et al. | |
| 6,361,543 B1 | 3/2002 | Chin et al. | |
| 6,371,910 B1 * | 4/2002 | Zwart et al. | 600/207 |
| 6,371,964 B1 | 4/2002 | Vargas et al. | |
| 6,478,029 B1 | 11/2002 | Boyd et al. | |
| 6,500,194 B2 * | 12/2002 | Benderev et al. | 606/232 |
| 6,508,252 B1 | 1/2003 | Berg et al. | |
| 6,508,826 B2 | 1/2003 | Murphy et al. | |
| 6,517,563 B1 | 2/2003 | Paolitto et al. | |
| 6,592,515 B2 | 7/2003 | Thierfelder et al. | |
| 6,603,051 B1 * | 8/2003 | Beaudry | 602/41 |
| 6,605,037 B1 | 8/2003 | Moll et al. | |
| 6,613,055 B2 | 9/2003 | Di Emidio et al. | |
| 6,656,109 B2 | 12/2003 | DeVries et al. | |
| 6,663,562 B2 | 12/2003 | Chang | |
| 6,666,846 B1 | 12/2003 | Turovskiy et al. | |
| 6,689,103 B1 | 2/2004 | Palasis | |
| 6,712,795 B1 | 3/2004 | Cohen | |
| 6,730,020 B2 * | 5/2004 | Peng et al. | 600/201 |
| 6,786,898 B2 | 9/2004 | Guenst | |
| 6,830,546 B1 | 12/2004 | Chin et al. | |
| 6,890,295 B2 | 5/2005 | Michels et al. | |
| 6,936,005 B2 | 8/2005 | Poff et al. | |
| 6,986,774 B2 | 1/2006 | Middleman et al. | |
| 7,063,693 B2 | 6/2006 | Guenst | |
| 7,112,172 B2 * | 9/2006 | Orban et al. | 600/209 |
| 7,122,003 B2 | 10/2006 | Nakao | |
| 7,666,199 B2 * | 2/2010 | McIntyre | 606/158 |
| 2001/0009987 A1 | 7/2001 | Moshe et al. | |
| 2001/0034527 A1 | 10/2001 | Scribner et al. | |
| 2001/0037053 A1 | 11/2001 | Bonadio et al. | |
| 2001/0051822 A1 | 12/2001 | Stack et al. | |
| 2002/0010388 A1 | 1/2002 | Taylor et al. | |
| 2002/0010389 A1 | 1/2002 | Butler et al. | |
| 2002/0022770 A1 | 2/2002 | Borsody | |
| 2002/0022845 A1 | 2/2002 | Zdeblick et al. | |
| 2002/0038128 A1 | 3/2002 | Turovkiy et al. | |
| 2002/0056460 A1 | 5/2002 | Boyd et al. | |
| 2002/0068923 A1 | 6/2002 | Caldwell et al. | |
| 2002/0069884 A1 | 6/2002 | Boyd et al. | |
| 2002/0074004 A1 | 6/2002 | Boyd et al. | |
| 2002/0077637 A1 | 6/2002 | Vargas et al. | |
| 2002/0087183 A1 | 7/2002 | Boyd et al. | |
| 2002/0091354 A1 | 7/2002 | Navia et al. | |
| 2002/0092533 A1 | 7/2002 | Boyd et al. | |
| 2002/0099270 A1 | 7/2002 | Taylor et al. | |
| 2002/0099338 A1 | 7/2002 | Young | |
| 2002/0099447 A1 | 7/2002 | Mears et al. | |
| 2002/0143343 A1 | 10/2002 | Castro | |
| 2002/0151902 A1 | 10/2002 | Riedel et al. | |
| 2002/0156487 A1 * | 10/2002 | Gellman et al. | 606/139 |
| 2002/0161391 A1 | 10/2002 | Murphy et al. | |
| 2002/0162559 A1 | 11/2002 | Crook | |
| 2002/0177874 A1 | 11/2002 | Nicholas et al. | |
| 2002/0183594 A1 | 12/2002 | Beane et al. | |
| 2002/0188301 A1 | 12/2002 | Dallara et al. | |
| 2002/0193863 A1 | 12/2002 | Rourke et al. | |
| 2003/0032967 A1 | 2/2003 | Park et al. | |
| 2003/0040717 A1 | 2/2003 | Saulenas et al. | |
| 2003/0055319 A1 | 3/2003 | Chang | |
| 2003/0062051 A1 | 4/2003 | Rambo | |
| 2003/0065351 A1 | 4/2003 | Hess et al. | |
| 2003/0074015 A1 | 4/2003 | Nakao | |
| 2003/0078478 A1 | 4/2003 | Bonadio et al. | |
| 2003/0083621 A1 | 5/2003 | Shaw et al. | |
| 2003/0105486 A1 | 6/2003 | Murphy et al. | |
| 2003/0176771 A1 | 9/2003 | Pulford et al. | |
| 2003/0187376 A1 | 10/2003 | Rambo | |
| 2003/0191478 A1 | 10/2003 | Kortenbach et al. | |
| 2003/0192553 A1 | 10/2003 | Rambo | |
| 2003/0195519 A1 | 10/2003 | Zdeblick et al. | |
| 2003/0195544 A1 | 10/2003 | Hess et al. | |
| 2003/0220538 A1 * | 11/2003 | Jacquetin | 600/37 |
| 2004/0034351 A1 | 2/2004 | Sherman et al. | |
| 2004/0039453 A1 * | 2/2004 | Anderson et al. | 623/23.72 |
| 2004/0049100 A1 | 3/2004 | Butler et al. | |
| 2004/0068276 A1 | 4/2004 | Golden et al. | |
| 2004/0073090 A1 | 4/2004 | Butler et al. | |
| 2004/0082923 A1 | 4/2004 | Field | |
| 2004/0092796 A1 | 5/2004 | Butler et al. | |
| 2004/0097793 A1 | 5/2004 | Butler et al. | |
| 2004/0097949 A1 | 5/2004 | Bonutti | |
| 2004/0133222 A1 | 7/2004 | Tran et al. | |
| 2004/0138526 A1 | 7/2004 | Guenst | |
| 2004/0143167 A1 | 7/2004 | Branch et al. | |
| 2004/0147812 A1 | 7/2004 | Hamel | |
| 2004/0176665 A1 | 9/2004 | Branch et al. | |
| 2004/0199052 A1 | 10/2004 | Banik et al. | |
| 2004/0254426 A1 | 12/2004 | Wenchell | |
| 2004/0260153 A1 | 12/2004 | Pulford et al. | |
| 2004/0267303 A1 | 12/2004 | Guenst | |

| | | | |
|---|---|---|---|
| 2005/0043580 A1* | 2/2005 | Watschke et al. ............ 600/30 |
| 2005/0080435 A1 | 4/2005 | Smith et al. |
| 2005/0119640 A1 | 6/2005 | Sverduk et al. |
| 2005/0131391 A1 | 6/2005 | Chu et al. |
| 2005/0165449 A1 | 7/2005 | Cadeddu et al. |
| 2005/0192483 A1 | 9/2005 | Bonadio et al. |
| 2005/0203344 A1 | 9/2005 | Orban et al. |
| 2005/0240209 A1 | 10/2005 | Hamada |
| 2005/0245945 A1 | 11/2005 | Ewers et al. |
| 2005/0267336 A1 | 12/2005 | Bertolero et al. |
| 2005/0273129 A1 | 12/2005 | Michels et al. |
| 2006/0030884 A1 | 2/2006 | Yeung et al. |
| 2006/0036277 A1 | 2/2006 | Kieturakis et al. |
| 2006/0052799 A1 | 3/2006 | Middleman et al. |
| 2006/0106288 A1 | 5/2006 | Roth et al. |
| 2006/0122462 A1 | 6/2006 | Roth et al. |
| 2006/0151568 A1 | 7/2006 | Weller et al. |
| 2006/0189889 A1 | 8/2006 | Gertner |
| 2006/0200002 A1 | 9/2006 | Guenst |
| 2006/0229493 A1* | 10/2006 | Weiser et al. ............... 600/37 |
| 2006/0247678 A1 | 11/2006 | Weisenburgh et al. |
| 2006/0248678 A1 | 11/2006 | Park |
| 2006/0258899 A1 | 11/2006 | Gill et al. |
| 2006/0270911 A1 | 11/2006 | Voegele et al. |
| 2007/0049790 A1* | 3/2007 | Wagner et al. ............... 600/37 |
| 2007/0055095 A1* | 3/2007 | Chu et al. ..................... 600/37 |
| 2009/0137877 A1 | 5/2009 | Minnelli et al. |
| 2009/0198107 A1* | 8/2009 | Park et al. .................... 600/215 |

FOREIGN PATENT DOCUMENTS

| | | |
|---|---|---|
| EP | 410561 A1 | 1/1991 |
| EP | 449663 | 10/1991 |
| EP | 469524 A1 | 2/1992 |
| EP | 499457 A1 | 8/1992 |
| EP | 545540 A1 | 6/1993 |
| EP | 568296 A1 | 11/1993 |
| EP | 586516 A1 | 3/1994 |
| EP | 586555 A1 | 3/1994 |
| EP | 602757 A2 | 6/1994 |
| EP | 610099 | 8/1994 |
| EP | 613351 A1 | 9/1994 |
| EP | 613659 A1 | 9/1994 |
| EP | 630211 A1 | 12/1994 |
| EP | 636036 A1 | 2/1995 |
| EP | 654247 A1 | 5/1995 |
| EP | 698374 A2 | 2/1996 |
| EP | 720446 A1 | 7/1996 |
| EP | 734231 A1 | 10/1996 |
| EP | 746350 A1 | 12/1996 |
| EP | 786961 | 8/1997 |
| EP | 791330 A2 | 8/1997 |
| EP | 810843 A1 | 12/1997 |
| EP | 835639 A2 | 4/1998 |
| EP | 843987 A1 | 5/1998 |
| EP | 875260 A2 | 11/1998 |
| EP | 888750 A1 | 1/1999 |
| EP | 906064 A1 | 4/1999 |
| EP | 956060 A1 | 11/1999 |
| EP | 981302 A1 | 3/2000 |
| EP | 983024 | 3/2000 |
| EP | 1125552 A1 | 8/2001 |
| EP | 1171040 | 1/2002 |
| EP | 1177772 A1 | 2/2002 |
| EP | 1208865 A2 | 5/2002 |
| EP | 1312318 A1 | 5/2003 |
| EP | 1472982 A2 | 11/2004 |
| EP | 1498079 | 1/2005 |
| EP | 1698272 | 9/2006 |
| EP | 1698293 | 9/2006 |
| WO | WO-9106261 A1 | 5/1991 |
| WO | WO-9211811 | 7/1992 |
| WO | WO-9219294 A1 | 11/1992 |
| WO | WO-9221292 A2 | 12/1992 |
| WO | WO-9221294 A1 | 12/1992 |
| WO | WO-9309709 | 5/1993 |
| WO | WO-9309722 A1 | 5/1993 |
| WO | WO-9311811 A1 | 6/1993 |
| WO | WO-9317625 A1 | 9/1993 |
| WO | WO-9320755 A1 | 10/1993 |
| WO | WO-9320866 A1 | 10/1993 |
| WO | WO-9322973 A1 | 11/1993 |
| WO | WO-9325148 A1 | 12/1993 |
| WO | WO-9403114 A1 | 2/1994 |
| WO | WO-9416630 A1 | 8/1994 |
| WO | WO-9422384 A1 | 10/1994 |
| WO | WO-9424947 A1 | 11/1994 |
| WO | WO-9501193 A1 | 1/1995 |
| WO | WO-9502988 A2 | 2/1995 |
| WO | WO-9508952 A1 | 4/1995 |
| WO | WO-9515723 A1 | 6/1995 |
| WO | WO-9522289 A2 | 8/1995 |
| WO | WO-9602195 A1 | 2/1996 |
| WO | WO-9610430 A2 | 4/1996 |
| WO | WO-9620749 A1 | 7/1996 |
| WO | WO-9624291 A1 | 8/1996 |
| WO | WO-9640354 A1 | 12/1996 |
| WO | WO-9700049 A1 | 1/1997 |
| WO | WO-9707741 A1 | 3/1997 |
| WO | WO-9707742 A1 | 3/1997 |
| WO | WO-9725940 A1 | 7/1997 |
| WO | WO-9730666 A2 | 8/1997 |
| WO | WO-9732514 A2 | 9/1997 |
| WO | WO-9742893 A1 | 11/1997 |
| WO | WO-9802102 A1 | 1/1998 |
| WO | WO-9817208 A2 | 4/1998 |
| WO | WO-9824374 A1 | 6/1998 |
| WO | WO-9827869 A1 | 7/1998 |
| WO | WO-9834569 A1 | 8/1998 |
| WO | WO-9835714 A1 | 8/1998 |
| WO | WO-9848724 A1 | 11/1998 |
| WO | WO-9855029 A1 | 12/1998 |
| WO | WO-9903416 A1 | 1/1999 |
| WO | WO-9905976 A1 | 2/1999 |
| WO | WO-9909892 A1 | 3/1999 |
| WO | WO-9912477 A1 | 3/1999 |
| WO | WO-9912481 A1 | 3/1999 |
| WO | WO-9915226 A1 | 4/1999 |
| WO | WO-9921484 A2 | 5/1999 |
| WO | WO-9937345 A1 | 7/1999 |
| WO | WO-9938440 A1 | 8/1999 |
| WO | WO-9952445 A1 | 10/1999 |
| WO | WO-9952448 A1 | 10/1999 |
| WO | WO-9962457 A1 | 12/1999 |
| WO | WO-0001293 A2 | 1/2000 |
| WO | WO-0009024 A1 | 2/2000 |
| WO | WO-0010466 A1 | 3/2000 |
| WO | WO-0024326 A1 | 5/2000 |
| WO | WO-0032116 A1 | 6/2000 |
| WO | WO-0054675 A1 | 9/2000 |
| WO | WO-0061011 A1 | 10/2000 |
| WO | WO-0061035 A1 | 10/2000 |
| WO | WO-0062845 A1 | 10/2000 |
| WO | WO-0069346 A1 | 11/2000 |
| WO | WO-0069368 A2 | 11/2000 |
| WO | WO-0071033 A1 | 11/2000 |
| WO | WO-0078246 A2 | 12/2000 |
| WO | WO-0108581 A2 | 2/2001 |
| WO | WO-0124682 A2 | 4/2001 |
| WO | WO-0126558 A1 | 4/2001 |
| WO | WO-0126559 A1 | 4/2001 |
| WO | WO-0134228 A1 | 5/2001 |
| WO | WO-0160262 A1 | 8/2001 |
| WO | WO-0209591 A2 | 2/2002 |
| WO | WO-0222053 A2 | 3/2002 |
| WO | WO-0239880 A2 | 5/2002 |
| WO | WO-02058993 A1 | 8/2002 |
| WO | WO-02076308 A2 | 10/2002 |
| WO | WO-02087652 A2 | 11/2002 |
| WO | WO-03000142 A2 | 1/2003 |
| WO | WO-03015855 A1 | 2/2003 |
| WO | WO-03028523 A2 | 4/2003 |
| WO | WO-03070085 A2 | 8/2003 |
| WO | WO-03077726 A2 | 9/2003 |
| WO | WO-03090644 A1 | 11/2003 |
| WO | WO-03094744 A1 | 11/2003 |
| WO | WO-03094754 A1 | 11/2003 |
| WO | WO-03096851 A1 | 11/2003 |
| WO | WO-03101314 A1 | 12/2003 |

| | | |
|---|---|---|
| WO | WO-03103548 A1 | 12/2003 |
| WO | WO-2004011037 A2 | 2/2004 |
| WO | WO-2004016186 A1 | 2/2004 |
| WO | WO-2004016299 A2 | 2/2004 |
| WO | WO-2004026153 A1 | 4/2004 |
| WO | WO-2004026371 A2 | 4/2004 |
| WO | WO-2004030547 A1 | 4/2004 |
| WO | WO-2004041148 A1 | 5/2004 |
| WO | WO-2004050138 A2 | 6/2004 |
| WO | WO-2004052178 A2 | 6/2004 |
| WO | WO-2004071312 A1 | 8/2004 |
| WO | WO-2004075741 A2 | 9/2004 |
| WO | WO-2004096012 A2 | 11/2004 |
| WO | WO-2004096060 A2 | 11/2004 |
| WO | WO-2004098395 A1 | 11/2004 |
| WO | WO-2004103161 A2 | 12/2004 |
| WO | WO-2004110263 A1 | 12/2004 |
| WO | WO-2005009257 | 2/2005 |
| WO | WO-2005056099 | 6/2005 |
| WO | WO-2005058239 | 6/2005 |
| WO | WO-2005089433 | 9/2005 |
| WO | WO-2006044797 | 4/2006 |
| WO | WO-2006055804 | 5/2006 |
| WO | WO-2006057702 | 6/2006 |
| WO | WO-2006072008 | 7/2006 |
| WO | WO-2006113394 | 10/2006 |

OTHER PUBLICATIONS

Abu-Rafea, B. et al. "Effect of body habitus and parity on insufflated $CO_2$ volume at various intraabdominal pressures during laparoscopic access in women," *Journal of Minimally Invasive Gynecology* (2006) 13, 205-210, Feb. 14, 2006.

Asao, T. et al. "Usefullness of a visceral mini-retractor accessible without trocar port during laparoscopic surgery," *Surgical Endoscopy* (1999) 13:91.

Landman, J. et al. "Application of a Fixed Retractor System to Facilitate Laparosocopic Radical Prostatectomy," *American Urological Association*, vol. 171, 783-785, Feb. 2004.

Product Facts: Omni-Lapo Tract® Scope and Instrument Holder, Product Specifications, Omni-Tract® Surgical, 2005.

Székely, G. et al. "Anatomical Model Generation for Laparoscopic Surgery Simulation." In the Second Visible Human Project Conference Proceedings, Bethesda, MA: National Library of Medicine, Oct. 1998.

Partial International Search Report, PCT/US2008/074276, Dec. 19, 2008, 5 pages.

International Search Report & Written Opinion, PCT/US2008/084475, Mailed Jun. 30, 2009, 15 pages.

* cited by examiner

TISSUE RETRACTORS

FIELD OF THE INVENTION

The present invention relates to methods and devices for manipulating tissue during surgical procedures.

BACKGROUND OF THE INVENTION

During certain surgical procedures, body tissue such as organs can obstruct an area a surgeon needs accessible for surgery. Relocating the tissue during all or part of the procedure can allow a surgeon to access an otherwise obstructed part of the body. The tissue may also need to be relocated to reduce chances of it being damaged as work is being done on another, nearby part of the body.

Tissue retractors have been developed that allow some movement of tissue in a body cavity during a surgical procedure. For example, a tissue retractor may be inserted into the body through an incision, and it can be used to push tissue aside to provide access to an underlying area. Current retractors include a rigid fan-type design, a spoon or fork-like device, or an inflatable bladder. While such tissue retractors can move tissue, they typically move small amounts of tissue and are difficult or impossible to keep in a fixed position during use without constant human interaction.

Accordingly, there remains a need for improved methods and devices for manipulating tissue.

SUMMARY OF THE INVENTION

The present invention generally provides methods and devices for performing various procedures using tissue retractors. In one embodiment, a surgical device is provided and includes a flexible fabric adapted to support tissue. At least one grasping element can be coupled to the flexible fabric, and it can be adapted to be manipulated to move the flexible fabric and thereby move the tissue. A deployment member can also optionally be coupled to the flexible fabric, and it can be adapted to allow the fabric to be pulled through a port.

The flexible fabric of the device can have a variety of configurations, but in one embodiment the flexible fabric is moveable between an open position, in which the flexible fabric is adapted to support tissue, and a closed or collapsed position, in which the flexible fabric is adapted to fit through a port. The flexible fabric can include at least one structural support adapted to provide structural integrity to the flexible fabric. In one embodiment, the structural support can be a rib extending along at least a portion thereof. The rib can be formed from, for example, a shape memory material. The flexible fabric can also be formed from a variety of materials, such as a mesh material, and it can have a variety of shapes, such as a substantially rectangular shape. In an exemplary embodiment, the flexible fabric can have a maximum width in a range of about 5 mm to 12 mm. In another embodiment, the flexible fabric can include at least one bladder formed therein, such as an inflatable bladder. The device can also include at least one inflation port formed in the flexible fabric and in communication with the bladder.

The deployment member can also have a variety of configurations, and in one embodiment it can be coupled to a mid-portion of the flexible fabric. The deployment member can be, for example, a ribbon. The grasping element can also have a variety of configurations, but in an exemplary embodiment it is one or more tethers coupled to a perimeter of the flexible fabric. Where the flexible fabric has a substantially rectangular shape, the grasping element can include four tethers coupled to four corners of the flexible fabric. In another embodiment, the grasping element can be at least one tab having an opening adapted to seat a rod for manipulating the flexible fabric.

In yet another embodiment, a surgical system is provided and includes a cannula having a proximal end and a distal end, a fabric disposed within the cannula, and a deployment member coupled to the fabric and extending from the distal end of the cannula such that the deployment member can be pulled distally to advance the fabric out of the distal end of the cannula to allow the fabric to support tissue. The system can also include at least one grasping element coupled to the fabric and extending from the proximal end of the cannula such that the at least one grasping element can be manipulated when the fabric is advanced distally from the cannula to move tissue supported by the fabric. The cannula can have a variety of sizes, but in an exemplary embodiment it can have a diameter in the range of about 10 mm to 15 mm.

In other aspects, a surgical method is provided and includes inserting a fabric through a port to position the fabric in a body cavity, positioning tissue, such as an organ, in the fabric such that the fabric supports the tissue, and manipulating at least one grasping element coupled to the fabric to move the tissue. Inserting the fabric can include pulling a deployment member coupled to the fabric from a distal end of the port to pull the fabric into the body cavity. The at least one grasping element can extend from a proximal end of the port, and it can be manipulated by pushing or pulling on the grasping element. A rod can optionally be used to push the grasping element.

In one embodiment, positioning the tissue in the fabric can include manipulating the at least one grasping element to move the fabric around the tissue. Alternatively, positioning the tissue in the fabric can include manipulating a grasper to grasp at least one of the tissue and the fabric to place the tissue in the fabric. In another embodiment, positioning tissue in the fabric can include inflating at least one bladder formed in the fabric.

In other aspects, the at least one grasping element can be disposed within the body cavity, and the method can further include, prior to manipulating, capturing the at least one grasping element and pulling the at least one grasping element through a tissue surface such that the at least one grasping element can be anchored percutaneously. The method can also include clamping the at least one grasping element to maintain the fabric and the tissue contained therein in a fixed position.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
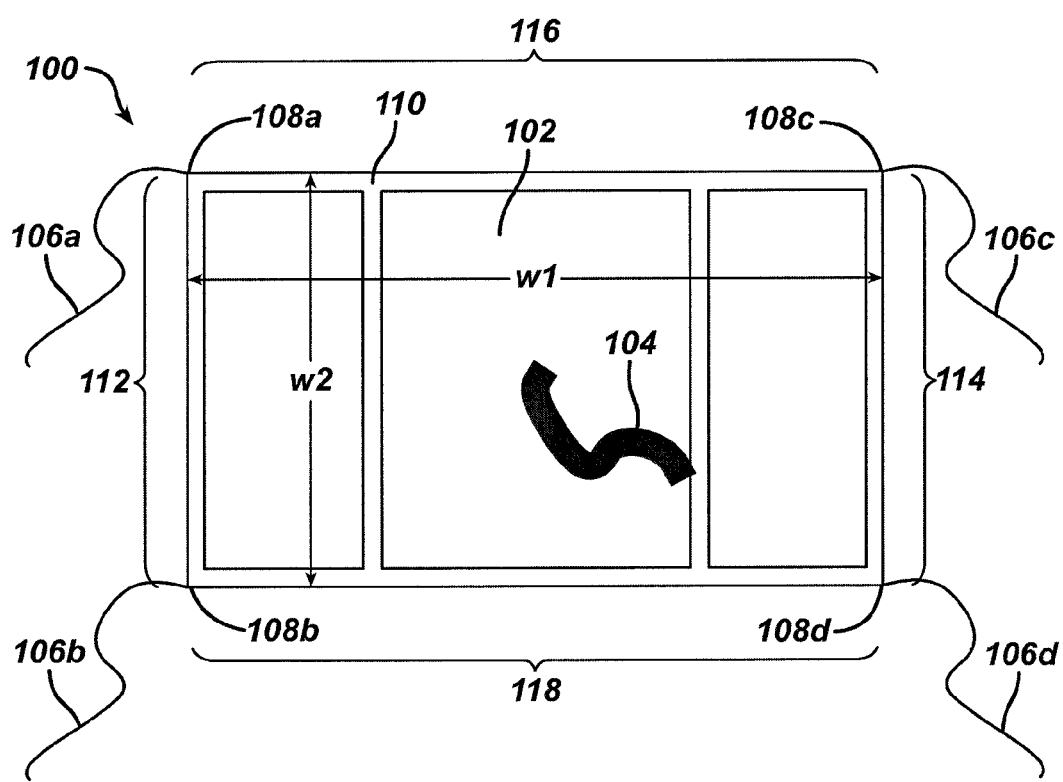
FIG. 1 is a schematic diagram of an embodiment of a retractor having ribs formed thereon.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for performing surgical procedures using tissue retractors. In general, the methods and devices allow a surgeon to use a retractor to capture a large or small amount of tissue in a fabric and to move the fabric to relocate the tissue to one or more convenient locations during the procedure. The flexible nature of the fabric can allow the fabric to be moveable between an open position, in which the fabric can support tissue, and a closed position, in which the fabric can be folded, rolled, or otherwise compressed in size and fit through a port, e.g., a trocar or an incision in a tissue wall. Once the retractor is inside the body, the need to repeatedly position tissue during a procedure can be reduced because more than a small amount of tissue can be held in the fabric and moved at a time. The flexible nature of the fabric can allow more freedom of movement in positioning the fabric within the body and in moving the tissue rather than a retractor made of non-flexible material, such as metal. Additionally, holding and moving tissue in a fabric retractor can reduce the chances of the tissue slipping or sliding away from the retractor, a common occurrence when using rigid retractors. This also reduces the need for tissue reengaging and repositioning. Furthermore, the position of the fabric and thus the tissue held in the fabric can be easily adjusted and readjusted by pushing or pulling one or more grasping elements coupled to the fabric. The fabric can also be anchored in place through a port, such as a trocar or a tissue wall, using one or more anchoring elements, thereby reducing the chances of the fabric and thus any tissue it holds from slipping or sliding away from a desired position.

A person skilled in the art will appreciate that the devices disclosed herein can be used in numerous surgical procedures and in connection with numerous body cavities and body tissues. For example, the devices can be used in procedures that take place in the abdominal, thoracic, pelvic, and abdominopelvic cavities, and they can be used to move any tissue, including organs such as the bowel, small intestine, stomach, liver, uterus, etc. The devices can be introduced into the body in any way in any of the procedures, such as through an incision or percutaneously through an access device.

A person skilled in the art will also appreciate that the particular configuration and materials of the retractor can vary depending on factors such as the type of procedure being performed and the type of tissue being relocated. The retractor can have any shape with any number of sides and curves, e.g., rectangular, elliptical, hexagonal, trapezoidal, etc. The retractor can also be made from any flexible fabric material appropriate for surgical use and can include zero, one, or more structural supports, e.g., ribs, inflatable bladders, etc. Grasping elements coupled to the retractor can be of any number, configuration on the fabric, and style (e.g., tethers, deployment members, tabs, etc.).

FIG. 1 illustrates one embodiment of a retractor 100 having a fabric 102 that can hold tissue during a surgical procedure. The substantially rectangular shaped fabric 102 as shown includes a deployment member 104 coupled to its midsection and four tethers 106a, 106b, 106c, 106d. The tethers 106a-d are coupled to each of the fabric's four corners 108a, 108b, 108c, 108d, although the fabric 102 could include any number of tethers at any location on the fabric 102. The fabric 102 also has inlaid ribs 110 that can provide structural integrity to the fabric 102. In use, the fabric 102 can be pulled by the deployment member 104 into a body cavity through a port, such as an incision or a trocar. Once inside the body, the fabric 102 can be manipulated to receive, hold, move, and release tissue by grasping and pulling (including tightening and slackening) one or more grasping elements, such as the deployment member 104 and/or the tethers 106a-d.

The fabric 102 can have a variety of configurations that allow the fabric 102 to hold tissue and temporarily move tissue to another location during a surgical procedure. In the illustrated embodiment, the fabric 102 has a substantially rectangular shape having a first width w1 extending between shorter length sides 112, 114 that is greater than a second width w2 extending between longer length sides 116, 118. However, the fabric 102 can have any shape, e.g., rectangular (including square), elliptical (including circular), hexagonal, trapezoidal, etc. The fabric 102 can also have a two dimensional shape when in an open configuration as shown, but in other embodiments the fabric 102 can have a third dimension. For example, the fabric's shape in an open position can be cone-shaped, domed, elliptical (similar to a parachute), or prism-shaped with one or more sides of the prism missing so as to allow tissue to be held in the fabric 102.

The fabric 102 can also have a variety of sizes, and different sizes of the fabric 102 may be appropriate for relocation of different types of tissue, i.e., a larger fabric for moving the liver than for moving the stomach. Preferably, the fabric 102 has dimensions that allow it to fit inside a commercially available cannula so that, as further described below, the fabric 102 can be introduced into a body through the cannula.

The tethers 106a-d attached to the fabric 102 can also have any structure. For example, the tethers 106a-d can include any combination of threads, strings, ribbons, cords, rods, loops, and other similar structures. One or more of the tethers 106a-d can include a loop of any size at its terminal-most or free end or elsewhere along its length such that fingers or surgical instruments can grasp a tether by engaging the loop. The tethers 106a-d can also have any length and width. Preferably, the tethers 106a-d are long enough to extend from a body cavity and out of the body, as further discussed below, thereby allowing the tethers 106a-d to be manipulated from outside the body when receiving, releasing, or moving tissue in the fabric 102.

As indicated above, the tethers 106a-d can be used for pulling the fabric 102 when introducing the fabric 102 into a body cavity, when receiving tissue in or releasing tissue from the fabric 102, and when moving tissue held in the fabric 102. Any number of tethers 106a-d can be coupled to the fabric 102 in any configuration, and the tethers 106 can be coupled to the fabric 102 at any point or points along its perimeter or elsewhere on its surface. Preferably, there are at least two tethers coupled to the fabric 102 to provide adequate tension when grasping tethers in moving or securing the fabric 102. The tethers 106a-d can be separate, or they can be integrally formed. For example, FIG. 1 illustrates a single string having two ends that form two tethers 106a, 106b and another single string that forms two tethers 106c, 106d. Each string can be mated to or inlaid along the shorter sides 112, 114 of the fabric 102.

The tethers 106a-d can be coupled to the fabric 102 using various techniques. For example, as indicated above, the tethers 106a-d can be inlaid along a length of the fabric 102 and overhang as one or more tethers, such as here at the corners 108a-d. In other embodiments, the tethers 106a-d can be integrally formed with the fabric 102, included as part of the fabric 102 (i.e., tethers of fabric extending from one or more places along the fabric's perimeter), or otherwise coupled to the fabric 102. The tethers 106a-d are preferably permanently coupled to the fabric 102, but one or more of the tethers 106a-d can be removable.

As indicated above, the retractor 100 can also include the deployment member 104 for pulling the fabric 102 into a body cavity. The deployment member 104 can also be used as a grasping element after the fabric 102 has been introduced to a body cavity. While the deployment member 104 is not necessary, using the deployment member 104 can make it easier to introduce the fabric 102 into a body cavity, particularly when the fabric 102 is introduced through a cannula.

The deployment member 104 can have any structure. For example, the deployment member 104 can be formed from threads, strings, ribbons, cords, rods, loops, and other similar structures, or combinations thereof. The deployment member 104 can include a loop of any size at its terminal-most or free end or elsewhere along its length such that fingers or surgical instruments can grasp the deployment member 104 by engaging the loop. The deployment member 104 can also have any length and width. Preferably, the deployment member 104 should be long enough to extend out of a cannula, as further discussed below, when the fabric 102 is inside a cannula before introduction into a body.

Any number of deployment members 104 can be coupled to the fabric 102 in any configuration, but in an exemplary embodiment, the retractor 100 includes one deployment member 104. The deployment member 104 is preferably coupled to a mid-portion of the fabric 102 as shown on the retractor 100, but the deployment member 100 can be coupled to the fabric 102 at any location.

The deployment member 104 can be coupled to the fabric 102 in any way. For example, the deployment member 104 can be stitched to the fabric 102, included as part of the fabric 102 (i.e., ribbon of fabric extending from the fabric), or otherwise coupled to the fabric 102. The deployment member 104 is preferably permanently coupled to the fabric 102, but the deployment member 104 can be removable.

The fabric 102, the tethers 106a-d, and the deployment member 104 can each be made from any type of material appropriate for use in a body, such as mesh (braided or unbraided), fiber (natural or synthetic), gauze-like cloth, and other similar types of material. Braided mesh is preferred for the fabric 102 because tissue is generally less likely to stick or snag on braided mesh than on other materials. The tethers 106a-d and the deployment member 104 are each preferably made from synthetic fiber. Each of the tethers 106a-d is preferably made from the same material, but one or more of the tethers 106a-d can be made from a material different from one or more of the other tethers 106a-d. The fabric 102 can also be flexible, thereby providing easy maneuverability when introducing the fabric 102 to a body cavity and when manipulating the fabric 102 once inside the body. The tethers 106a-d and the deployment member 104 are preferably made from a non-elastic material, but they can be flexible or rigid.

The retractor 100 can also optionally include one or more structural members, such as ribs 110, for providing structural integrity to the fabric 102, thereby making it easier for a surgeon to gather tissue in the fabric 102, for tissue to stay in the fabric 102 once received there, and/or for the fabric 102 to substantially maintain its shape when anchored as further discussed below. In an exemplary embodiment, the ribs 110 are made from a shape memory material, such as Nitinol (a nickel-titanium alloy), but they can be made from any type of material able to provide structure to the fabric 102 and appropriate for use in the body. Other exemplary metallic materials include alloys such as copper-zinc-aluminum-nickel, copper-aluminum-nickel, and nickel-titanium. Additional exemplary non-metallic materials may include thermoplastic materials such as Nylon or Nylon blends and shape memory polymers such as Veriflex™. The fabric 102 can include any number of the ribs 110. The ribs 110 are shown as one interconnected rib in the illustrated embodiment, but the ribs 110 can include two or more independent ribs.

The ribs 110 can also have any configuration in the fabric 102. In the illustrated embodiment, the ribs 110 are coupled to the fabric 102 along a perimeter of the fabric 102 and in two spaced-apart lengths extending parallel to the shorter sides 112, 114 of the fabric 102. The ribs 110 can, however, be coupled to the fabric 102 in any configuration lengthwise, widthwise, and/or in one or more directions not parallel to any side of the fabric 102. The ribs 110 can also be coupled to the fabric's perimeter, in the fabric's interior, or both. A majority of the fabric's perimeter preferably has ribs to reduce chances of tissue slipping or sliding out of the fabric 102.

The ribs 110 are typically inlaid in the fabric 102 as shown in FIG. 1, but the ribs 110 can be coupled to the fabric 102 in one or more ways. For example, the ribs 110 can be sewn or mated to the fabric 102 such that the ribs 110 are fully or partially covered by the fabric 102. The ribs 110 can also be integrally formed on the fabric 102

Figure 2:
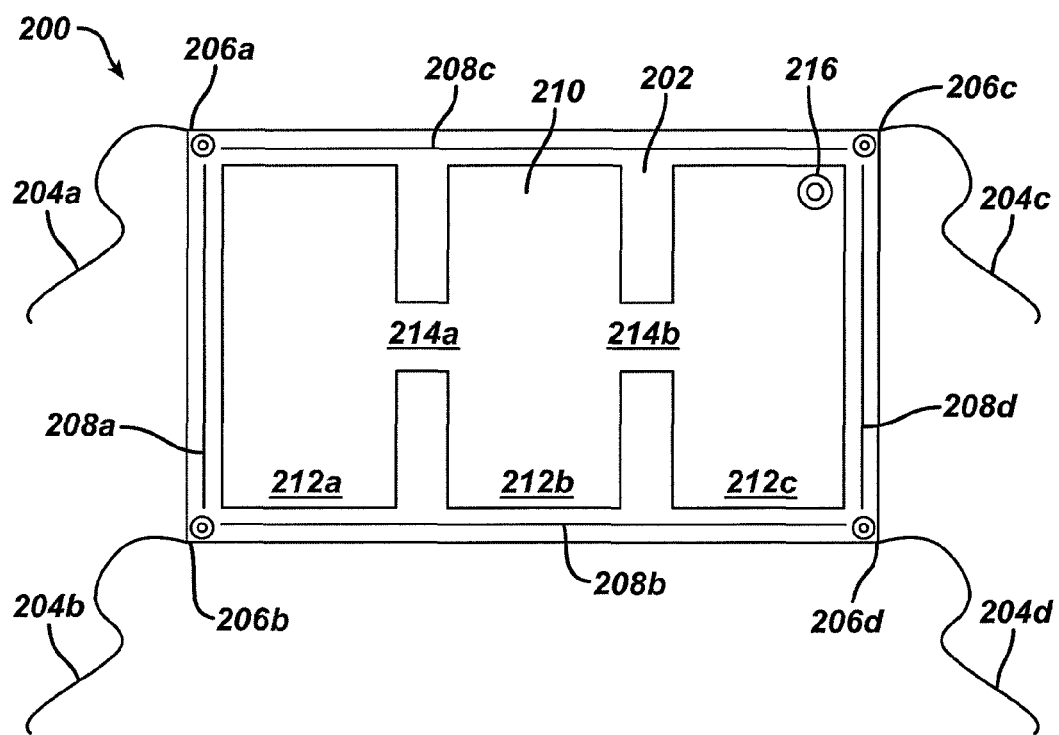
FIG. 2 is a schematic diagram of another embodiment of a retractor having several bladders formed therein.

FIG. 2 illustrates another embodiment of a retractor 200 that includes a fabric 202 that can hold tissue during a surgical procedure. The retractor 200 is similar to the retractor 100 of FIG. 1 and includes four tethers 204a, 204b, 204c, 204d coupled to each of four corners 206a, 206b, 206c, 206d of the substantially rectangular shaped fabric 202. The fabric 202 also includes ribs 208a, 208b, 208c, 208d inlaid along a majority of the fabric's perimeter. The fabric 202, the tethers 204a-d, and the ribs 208a-d are similar to those described with reference to similarly named elements included in FIG. 1.

In this embodiment, the fabric 202 includes a bladder 210 having a substantially rectangular shape with three substantially rectangular chambers 212a, 212b, 212c connected by two channels 214a, 214b, but the bladder 210 (and its chambers 212a-c and channels 214a-b) can have any shape. The bladder 210 can have any size, subject to the dimensions and flexibility of the fabric 202. If the bladder 210 includes more than one chamber and/or more than one channel, each chamber and each channel can have any size, different or the same from any other chamber or channel included in the bladder 210.

The bladder 210 can have a variety of configurations. For example, the bladder 210 can be formed in the fabric 202 as a cavity, e.g., two pieces of fabric can be mated together as discrete portions to create one or more cavities therein. The illustrated single cavity has three chambers 212a-c connected by two channels 214a-b, but the fabric 202 can include any number of bladders including one or more cavities connected by any number of channels (including zero channels). The left channel 214a connects the left chamber 212a with the middle chamber 212b, while the right channel 214b connects the middle chamber 212b with the right chamber 212c. In use, inflating fluid can be introduced into the bladder 210 through any one or more of the chambers 212a-c, and it can travel to one or more of the other chambers 212a-c via one or both of the channels 214a-b. Alternatively, the bladder 210 can include three unconnected cavities, and fluid can be separately introduced into each cavity to allow each cavity to be inflated to a selected size.

Fluid, such as air or saline (or any other gas or liquid), can be introduced to and drained from the bladder 210 through an inflation port 216 (e.g., a valve) formed in the fabric 202 and in communication with the bladder 210. In the illustrated embodiment, the right chamber 212c includes the inflation port 216 in one of its corners, but any of the chambers 212a-c could include the inflation port 216. Although the retractor 200 includes one inflation port 216, the tissue retractor 200 can include any number of inflation ports at any location on the fabric 202. If the tissue retractor 200 includes more than one bladder 210, each of the bladders 210 can have a dedicated inflation port 216. If the bladder 210 includes multiple chambers 212a-c, each bladder chamber 212a-c can have a dedicated inflation port 216 or, for chambers 212a-c connected by one or more channels 214a-b, there can be one inflation port 216 per two or more connected chambers 212a-c.

When the fabric 202 is inside a body and the bladder 210 is fully or partially inflated, the bladder 210 can provide increased rigidity to the fabric 202, thereby allowing the fabric 202 to more securely hold tissue and helping the fabric 202 to stay in a fixed position in the body. The bladder 210 also can be inflated to position tissue in the fabric 202. Because the fabric 202 includes the bladder 210, there can be a reduced need for other structural elements such as the ribs 208a-d, although one or more other structural elements such as the ribs 208a-d can be included in the retractor 200 to provide additional structural support to the fabric 202. When the bladder 210 is deflated, the fabric 202 can maintain a substantially flat configuration allowing the fabric 202 to be folded or otherwise compressed for easy introduction into, or removal out of, a body cavity.

Figure 3:
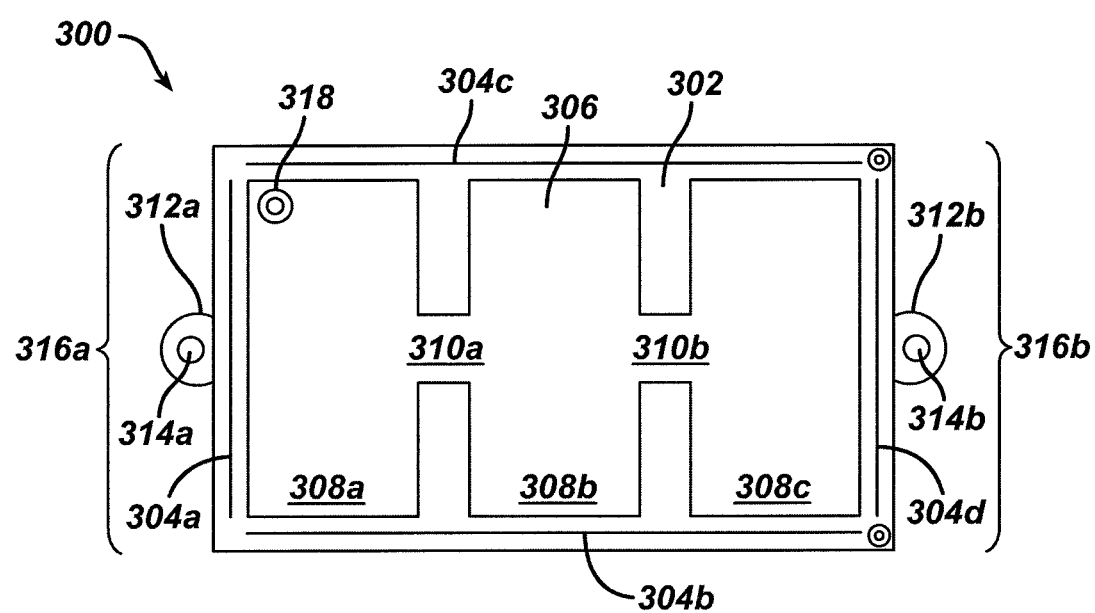
FIG. 3 is a schematic diagram of yet another embodiment of a retractor having tabs located thereon.

FIG. 3 illustrates another retractor 300 that includes a fabric 302 that can hold tissue during a surgical procedure. The retractor 300 includes ribs 304a, 304b, 304c, 304d inlaid along a majority of the fabric's perimeter. The fabric 302 includes a bladder 306 having three chambers 308a, 308b, 308c connected by two channels 310a, 310b. The bladder 306 can be inflated through an inflation port 318. The fabric 302, the ribs 304a-d, and the bladder 306 (including the chambers 308a-c, the channels 310a-b, and the inflation port 318) are similar to those described with reference to similarly named elements included in FIGS. 1 and 2.

In this embodiment, the retractor 300 includes tabs 312a, 312b that can be used as grasping elements, each having an opening 314a, 314b. The tabs 312a-b and the openings 314a-b can have any shape and size (length, width, depth), but preferably the shape and size is capable of receiving a rigid tool, such as a commercially available rod. Use with a rigid tool is particularly advantageous as it allows the tool to be used to push the tabs, thereby pushing the retractor, as opposed to tethers which are used to pull the retractor. The illustrated tabs 312a-b are coupled to the fabric 302 at mid-portions of short sides 316a, 316b of the rectangular shaped fabric 302, although the tabs 312a-b can be coupled to the fabric 302 at any location on the fabric 302 (preferably on the fabric's perimeter). Any number of tabs 312a-b can be coupled to the fabric 302 in any configuration, although the retractor 300 preferably includes at least two tabs 312a-b to provide adequate tension when moving or securing the fabric 302 with rods. In use, each of the openings 314a-b can be capable of seating a rod or other grasping device for manipulating the fabric 302. Rods seated in the tabs 312a-b can be pushed or pulled to move the fabric 302 to a particular position to gather or position tissue. The tabs 312a-b can be used alone or in addition to other grasping elements such as tethers.

Figure 4:
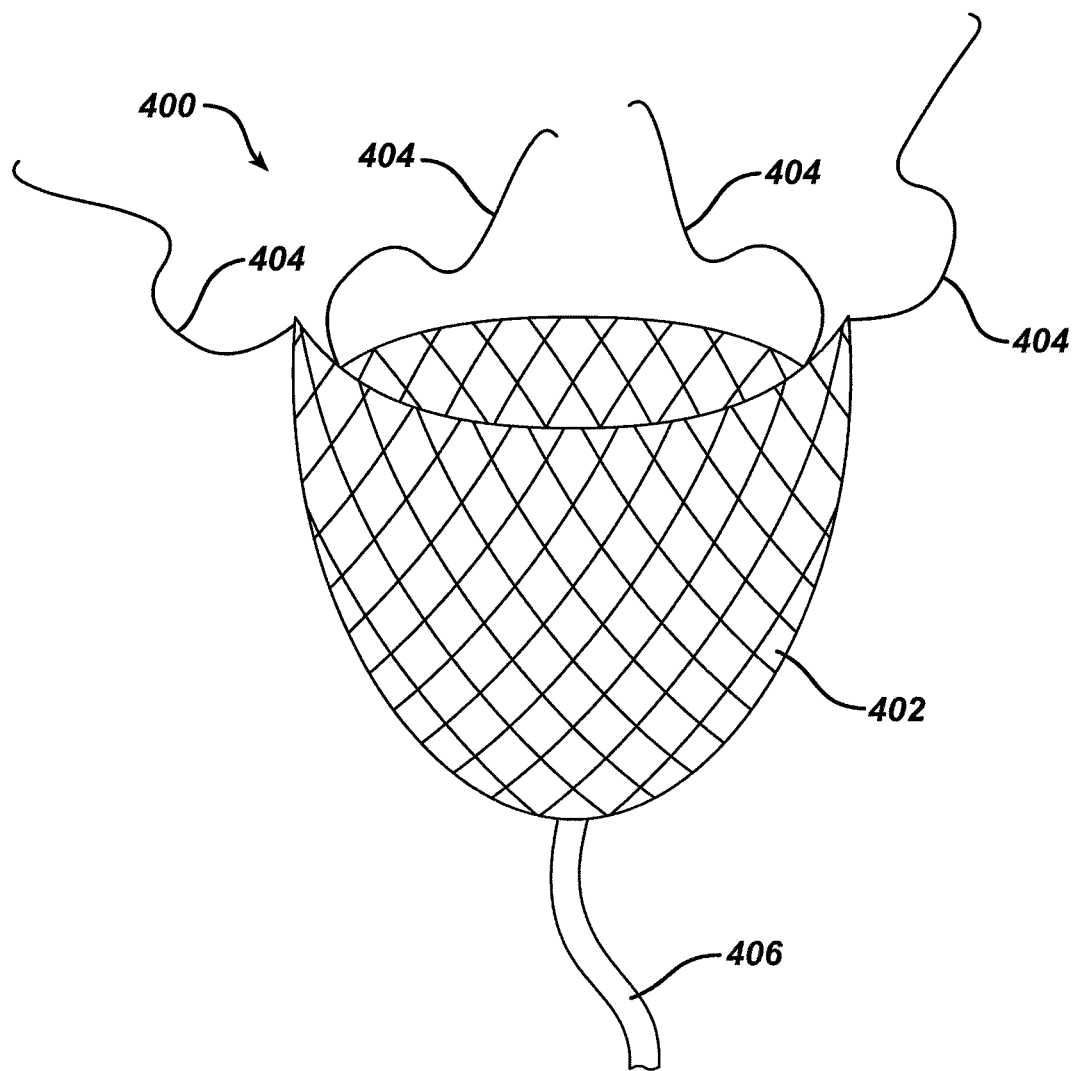
FIG. 4 is a perspective view of another embodiment of a retractor in a partially compressed position.

As indicated above, in use, the various retractors discussed herein can be moveable between an open position and a closed position. FIG. 4 illustrates a retractor 400 in a closed, partially compressed position. The retractor 400 includes a fabric 402 made of a flexible mesh material. Four tethers 404 and one deployment member 406 are coupled to the fabric 402. The retractor 400 is shown as if being held from above by the four tethers 404, with gravity "tenting" the fabric 402 in a downward direction and causing the deployment member 406 to dangle from a mid-portion of the fabric 402.

Figure 5:
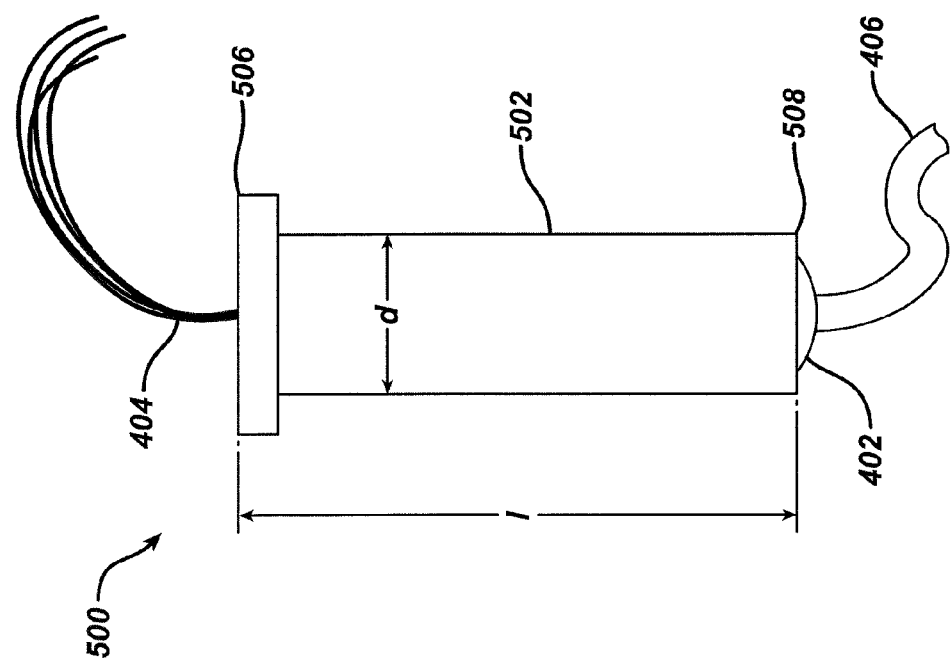
FIG. 5 is a side view of the retractor of FIG. 4 disposed in a cannula.

In one embodiment, in order to introduce the retractor 400 into a body cavity, the retractor 400 can be disposed within a cannula or other access port. FIG. 5 illustrates a retractor introduction system 500 that includes a cannula 502 having the retractor 400 of FIG. 4 disposed therein between a proximal end 506 of the cannula 502 and a distal end 508 of the cannula 502. The cannula 502 can have any configuration. For example, the cannula 502 can be a trocar cannula configured to receive an obturator or any other access device that provides a pathway through tissue to a body cavity. The size of the cannula 502 can also vary. In one exemplary embodiment, the cannula 502 is substantially cylindrical and is about 75 mm to 100 mm in length l with a diameter d of about 10 mm to 12 mm.

The fabric 402 is in a closed position, e.g., folded, rolled, or otherwise compressed, to fit through the cannula 502. The fabric 402 can partially extend from the proximal and/or distal end 506, 508 of the cannula 502, but the fabric 402 is preferably fully disposed in the cannula 502. Coupled to the fabric 402 and at least partially extending from the cannula 502 is the deployment member 406 and one or more grasping elements 404. When the fabric 402 is disposed in the cannula 502, the deployment member 406 extends from the distal end 508 of the cannula 502 such that the deployment member 406 can be pulled distally to advance the fabric 402 out of the distal end 508 of the cannula 502 to allow the fabric 402 to support tissue. The fabric 402 can instead or in addition be advanced out of the distal end 508 of the cannula 502 by pushing on the grasping elements 404 and/or the fabric 402 at the proximal end 506 of the cannula 502.

Figure 6:
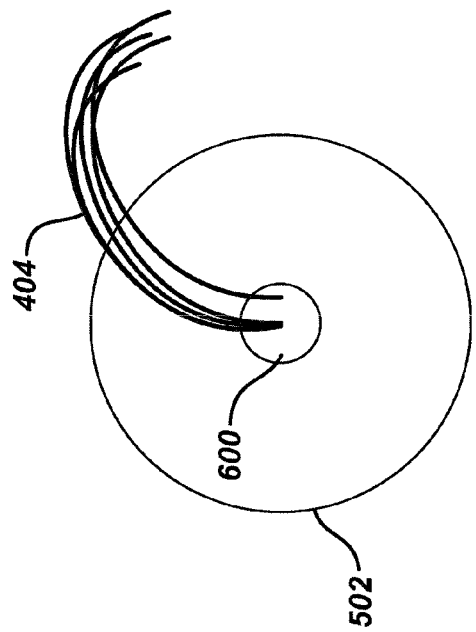
FIG. 6 is a top view of the retractor and cannula of FIG. 5.

As illustrated in FIG. 6, at least one of the grasping elements 404 coupled to the fabric 402 can extend through an opening 600 from the proximal end 506 of the cannula 502 such that the grasping element(s) 404 can be manipulated when the fabric 402 is advanced distally from the cannula 502 to hold tissue or move tissue supported by the fabric 402. The opening 600 can have any shape (e.g., elliptical, rectangular, etc.) and can be any size, although the opening 600 should be large enough to allow at least one of the grasping elements 404 to extend from the proximal end 506 of the cannula 502.

Figure 7:
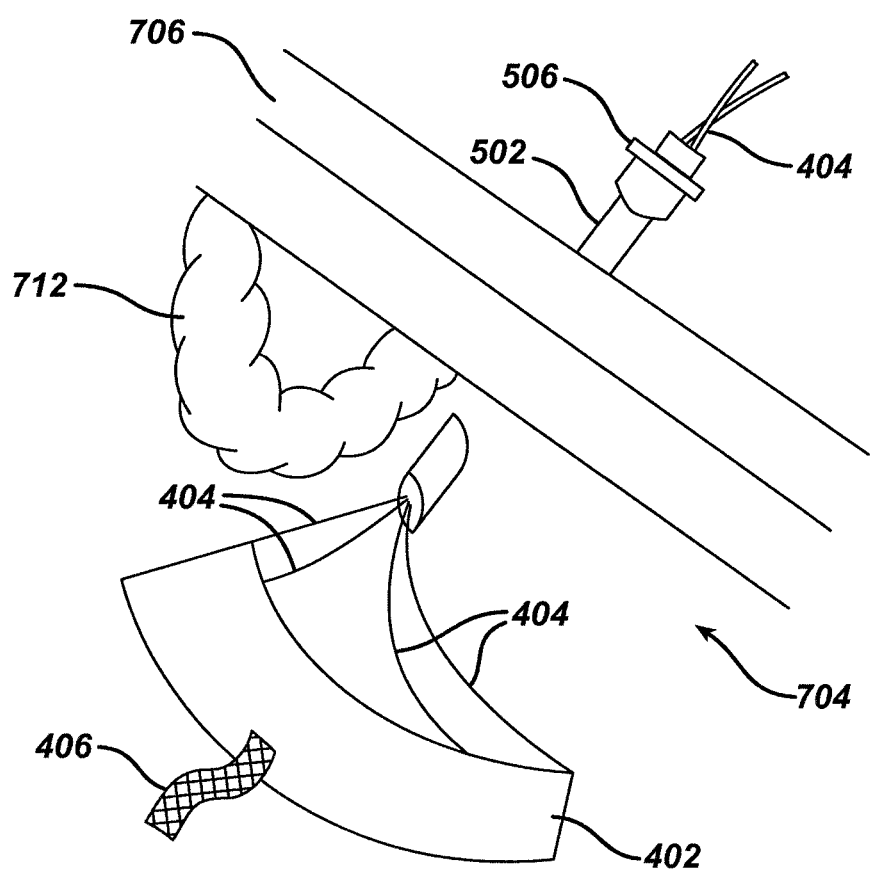
FIG. 7 is a perspective view of the retractor and cannula of FIG. 5 shown disposed through tissue.

With the retractor 400 disposed in the cannula 502, the cannula 502 can be introduced to a body cavity through a body wall. The fabric 402 can then be pulled through the cannula 502 to position the fabric 402 in the body cavity where it can hold and move tissue. FIG. 7 illustrates the retractor introduction system 500 of FIG. 5 in use extending from outside a body wall 706 (e.g., the abdominal wall) into a body cavity 704 (e.g., the abdomen). Although the retractor introduction system 500 of FIG. 5 is shown, the illustrated methods can be performed using any retractor disclosed herein or known in the art.

The cannula 502 can be inserted into the body cavity 704 in a variety of ways, such as through an incision made in the body wall 706. Although the cannula 502 is shown in a perpendicular position relative to the body wall 706, the cannula 502 can be at any angle and may move horizontally and/or vertically during use. With the distal end 508 of the cannula 502 disposed in the body cavity 704, the fabric 402 can be inserted into the body cavity 704 through the cannula 502 by advancing the fabric 402 distally. The fabric 402 can advance distally in a variety of ways. For example, the deployment member 406 extending from the distal end 508 of the cannula 502 can be pulled in a distal direction. Alternatively, one or more of the grasping elements 404 can be located at the distal end 508 of the cannula 502 and can be pulled in a distal direction. In yet another example, the fabric 402 can be pushed in a distal direction at the proximal end 506 of the cannula 502, e.g., through the opening 600 (see FIG. 6).

The fabric 402 can be introduced into the body cavity 704 in a closed position, but once partially or fully disposed in the body cavity 704, the fabric 402 can be moved to an open position able to support tissue. When the fabric 402 is in the body cavity 704, the grasping elements 404 can extend from the body cavity 704 through the cannula 502, and out the proximal end 506. Thus, one or more of the grasping elements 404 can be manipulated from outside the abdominal wall 706 to move the fabric 402 to a desired position and around a tissue 712. The portions of the grasping elements 404 located inside the body cavity 704 can also optionally be manipulated.

The cannula 502 may or may not be removed after the fabric 402 has been inserted into the body cavity 704. If removed, the grasping elements 404 can still extend between the body cavity 704 and outside the body wall 706 through one or more incisions.

Once the fabric 402 has been introduced into the body cavity 704, a surgeon can position the fabric 402 to hold the tissue 712. The fabric 402 can hold any amount of the tissue 712 and in any or all portions of the fabric 402. The tissue 712 can include more than one type of tissue, thereby allowing one retractor to simultaneously move multiple types of tissue. The tissue 712 can be held in more than one retractor, although only one fabric 402 is shown in the illustrated embodiment.

Figure 8:
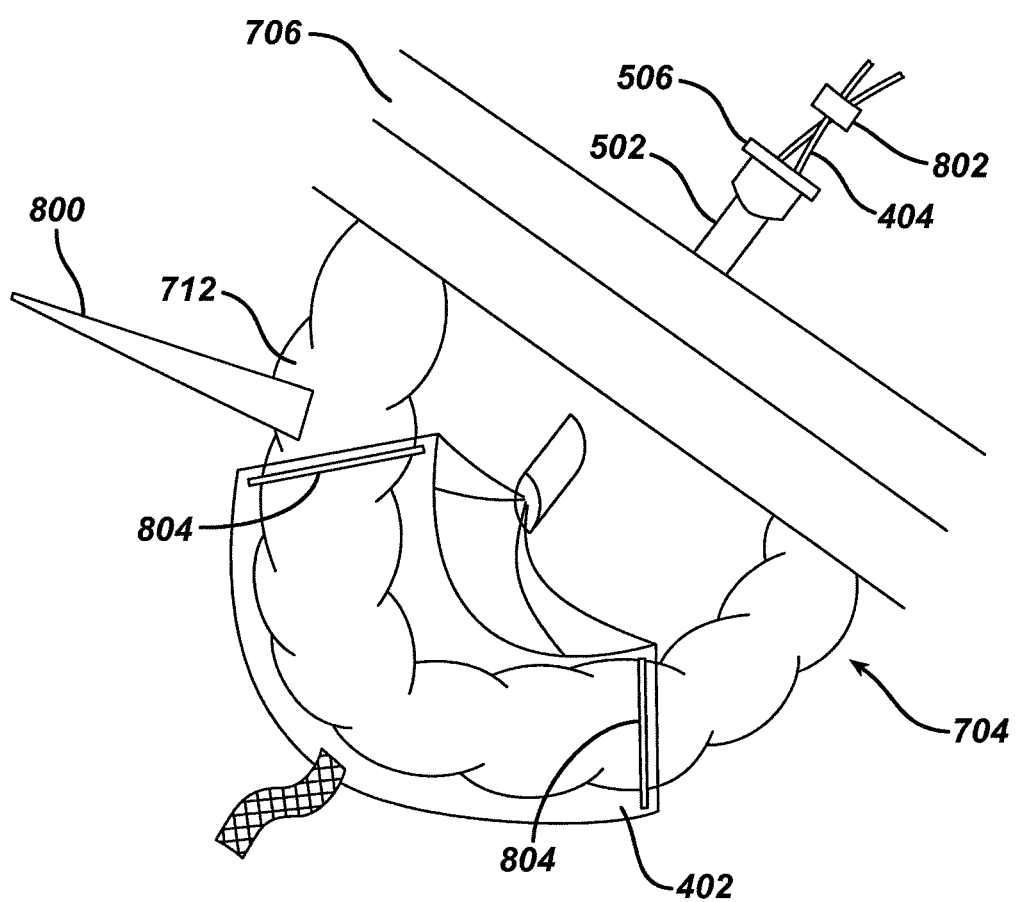
FIG. 8 is a perspective view of the retractor and cannula of FIG. 7 showing tissue positioned in the retractor.

Referring to FIG. 8, the tissue 712 is shown positioned in the fabric 402 such that the fabric 402 supports the tissue 712. The tissue 712 can be positioned in the fabric 402 in a variety of ways that can be performed alone or in any combination. For example, positioning the tissue 712 in the fabric 402 can include manipulating one of more of the grasping elements 404 (preferably from outside the body cavity 704) to move the fabric 402 around the tissue 712. One or more of the grasping elements 404 can be simultaneously or sequentially pulled to position the tissue 712 in the fabric 402 or to position the fabric 402 in a location proximate to the tissue 712. Gravity can move the tissue 712 from the proximate location to a position such that the tissue 712 can be supported by the fabric 402.

In another example, the tissue 712 can be positioned in the fabric 402 by manipulating a grasper to grasp at least one of the tissue 712 and the fabric 402 to place the tissue 712 in the fabric 402 or to place the fabric 402 around the tissue 712. Examples of graspers include fingers, hands, and any tool safe for surgical use and capable of grasping the tissue 712 and/or the fabric 402 such as forceps, rods, a spatula 800 as shown, and other similar tools. A grasper can grip the tissue 712 or push the tissue 712 to place it on or in a location proximate to the fabric 402. The fabric 402 can include one or more ribs 804 that can help position the tissue 712 in the fabric 402.

Figure 9:
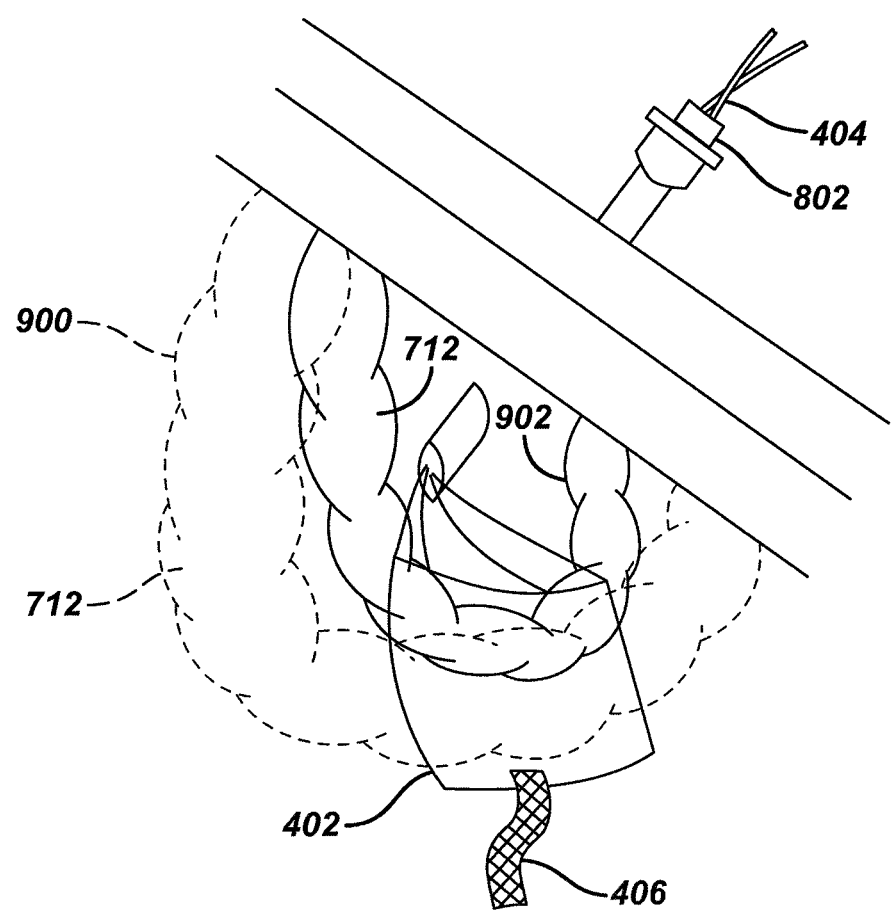
FIG. 9 is a perspective view of the retractor and cannula of FIG. 7 showing the retractor manipulated to move the tissue.

Once the fabric 402 supports a desired amount of the tissue 712, the fabric 402 can be manipulated to move the tissue 712. As shown in FIG. 9, the fabric 402 has been manipulated to move the tissue 712 supported by the fabric 402. The tissue 712 was moved from a first position 900 (the tissue 712 shown with dotted lines) to a second position 902 (the tissue 712 shown with solid lines). The two positions 900, 902 are examples; the tissue 712 can be moved in any direction and between any number of positions during any one surgical procedure.

The tissue 712 can be moved while supported by the fabric 402 in a variety of ways that can be performed alone or in combination. For example, manipulating at least one of the grasping elements 404 can include pulling at least one of the grasping elements 404 and/or the deployment member 406 to move the fabric 402. In another example, a hand or a surgical tool may pull the fabric 402.

Once moved to a desired position such as the second position 902, the fabric 402 can be fixed to anchor the fabric 402 and thus the tissue 712 in the second position 902. Fixing the fabric 402 can be accomplished by, for example, capturing one or more of the grasping elements 404 in a clamp 802 and engaging the clamp 802. Fixed in the second position 902, the tissue 712 can be held in that particular position with minimal or no human interaction during a surgical procedure. The fabric 402 can still be easily adjusted, e.g., by manipulating the grasping elements 404, by readjusting the clamp 802, by pulling the deployment member 406, etc.

Figure 9A:
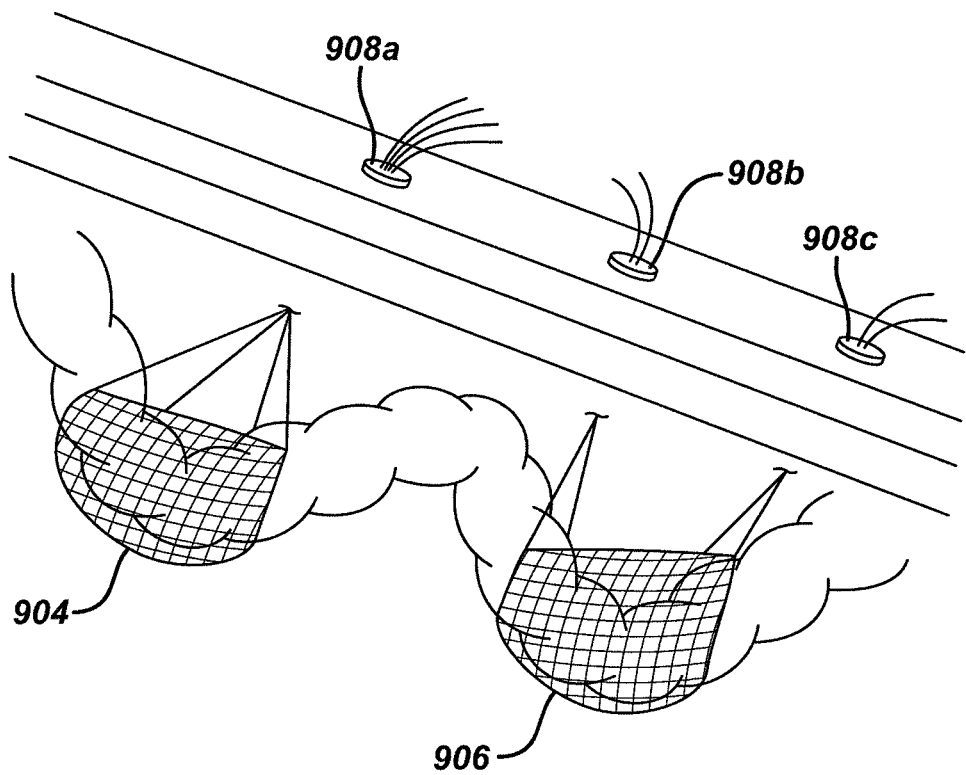
FIG. 9A is a perspective view of an embodiment of two retractors shown anchored percutaneously.

Once the tissue 712 is held in a desired position by the fabric 402, the tissue and the fabric 402 can be maintained in that position by using the clamp 802. For example, a surgeon can position the fabric 402 in a desirable location to receive or hold tissue, and the clamp 802 can be engaged to the grasping elements 404 to (temporarily) fix the fabric 402 in that location before or after the fabric 402 supports any of the tissue 712. The clamp 802 can have any size and any configuration. In this example, the clamp 802 is a spring-activated clamp, although any type of clamp 802 can be used to capture and hold the grasping elements 404. The clamp 802 can be attached to the grasping elements 404 before the fabric 402 is disposed in the cannula 502, before the fabric 402 is disposed in the body cavity 704, or at any point after the fabric's insertion into the body cavity 704. The clamp 802 should be large enough to prevent its passage through a port and into the body cavity 704, such as by having a size larger than the opening 600 of the cannula 502 (see FIG. 6). The clamp 802 could also be used to hold grasping elements 404 that extend directly through the tissue, e.g., through an incision in the abdominal wall, rather than through a cannula, as shown in FIG. 9A where two fabrics 904, 906 are percutaneously clamped using clamps 908a, 908b, 908c. Although only one clamp 802 is shown in FIG. 9, any number of clamps can be used with any one tissue retractor, e.g., a separate clamp for each of the grasping elements 404 (e.g., the clamps 908a, 908b, 908c in FIG. 9A). In other embodiments, a knot can be tied using one or more tether grasping elements 404.

Figure 10:
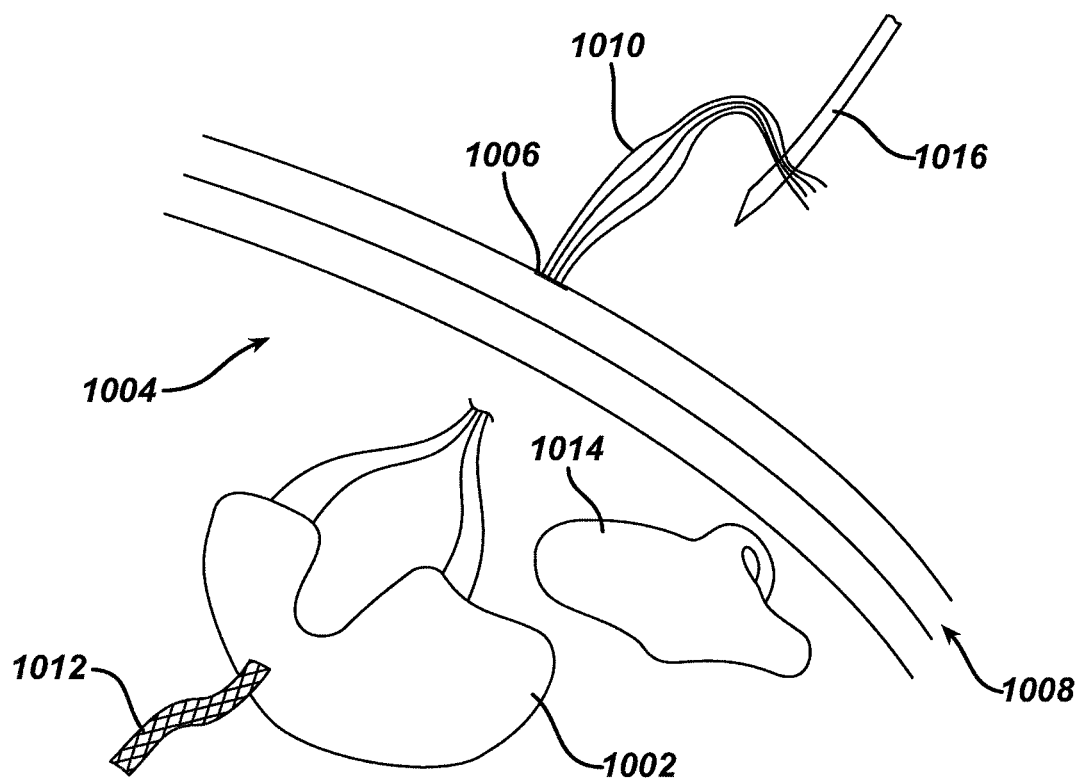
FIG. 10 is a perspective view of another embodiment of a retractor shown anchored percutaneously.

In another embodiment shown in FIG. 10, a fabric 1002 can be introduced into a body cavity 1004 at a first location, and grasping elements 1010 can be removed from the body cavity 1004 at a second location 1006 to enable manipulation of the grasping elements 1010. However, one or more of the tethers 1010 may not extend outside a body wall 1008 at any time during a surgical procedure. Preferably, at least one of the tethers 1010 is extended outside the body wall 1008 through the incision 1006 to allow one or more of the tethers 1010 to be anchored outside the body wall 1008 while positioning a tissue 1014 in the fabric 1002 or after moving the tissue 1014 held in the fabric 1002.

Inserting the fabric 1002 into the body cavity 1004, positioning the tissue 1014 in the fabric 1002, and moving the fabric 1002 and the tissue 1014 it supports can be accomplished as described above. The fabric 1002 can also be pushed through the incision 1006 from outside the body wall 1008. Additionally, a grasper 1016 can be used to grasp one or more of the tethers 1010, alone or in some combination, to pull the tethers 1010 through the incision 1006.

Figure 11:
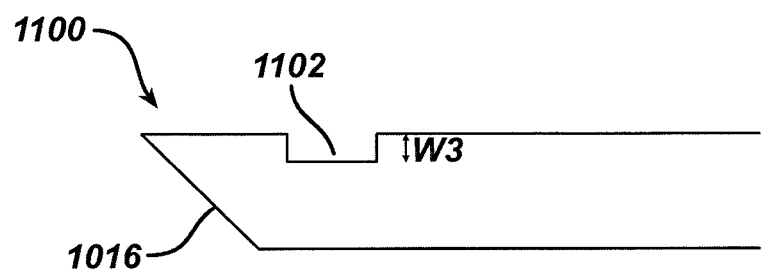
FIG. 11 is a perspective view of the grasper of FIG. 10.

The grasper 1016 can have any size and any configuration. FIG. 11 illustrates one embodiment of a grasper 1016 having a notch 1102 formed therein. The notch 1102 can be used to capture elements such as the tethers 1010 and/or a deployment member 1012. The notch 1102 has a width W3, which is typically larger than a width of at least one of the tethers 1010 to facilitate capturing the tethers 1010. The notch 1102 has a rectangular shape in this example, but the notch 1102 can have any shape.

In use, the grasper 1016 can pull the tethers 1010, the deployment member 1012, the fabric 1002, and/or the tissue 1014. The grasper 1016 can also be used to capture one or more of the tethers 1010, as shown in FIG. 10, and pull the captured tethers 1010 through the body wall 1008 so that the tethers 1010 can be grasped and manipulated.

Figure 12:
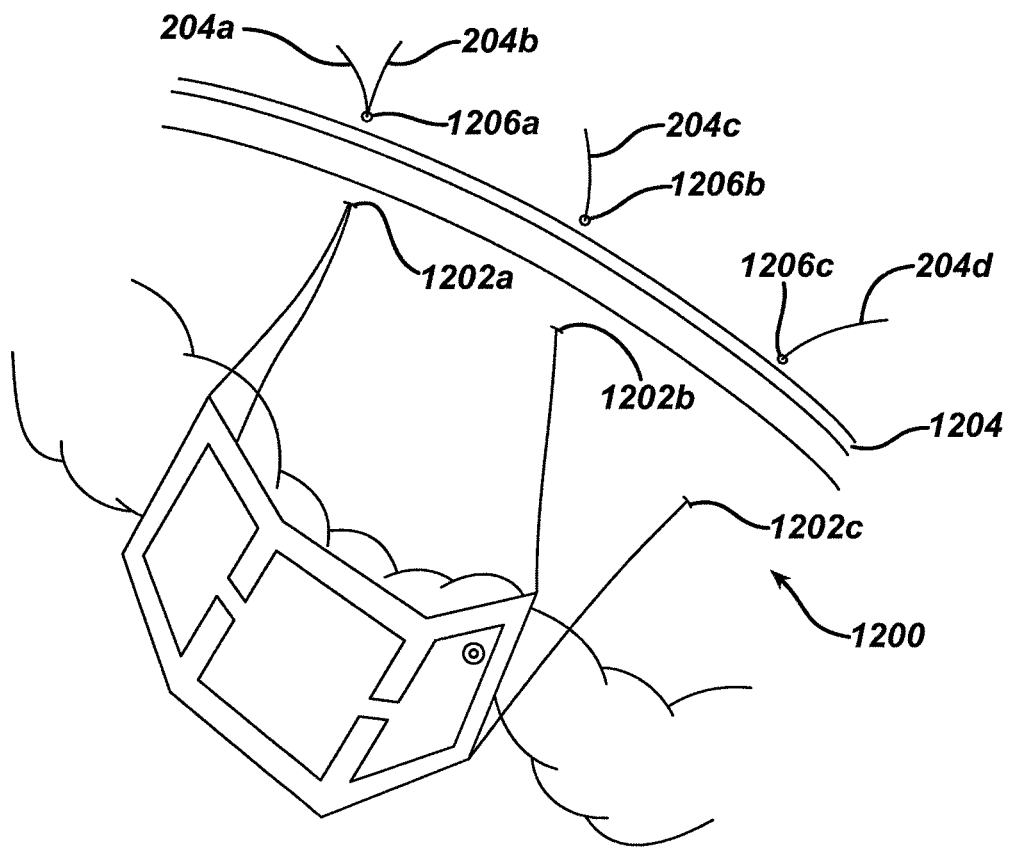
FIG. 12 is a perspective view of the retractor of FIG. 2 shown in use positioned within a body cavity.

In another embodiment, one or more of the grasping elements can extend outside the body cavity through more than one port. One of these ports can optionally be the one through which the fabric was introduced to the body cavity. FIG. 12 illustrates the retractor 200 of FIG. 2 where the fabric's four tethers 204a-d extend outside a body cavity 1200 through three ports 1202a, 1202b, 1202c in a body wall 1204. In particular, two tethers 204a, 204b extend through one incision 1202a, the tether 204c extends through another incision 1202b, and the tether 204d extends through a third incision 1202c. The tethers 204a-d can each be anchored at their respective incisions 1202a-c outside the body wall 1204 using clamps 1206a, 1206b, 1206c or other anchoring techniques.

Figure 13:
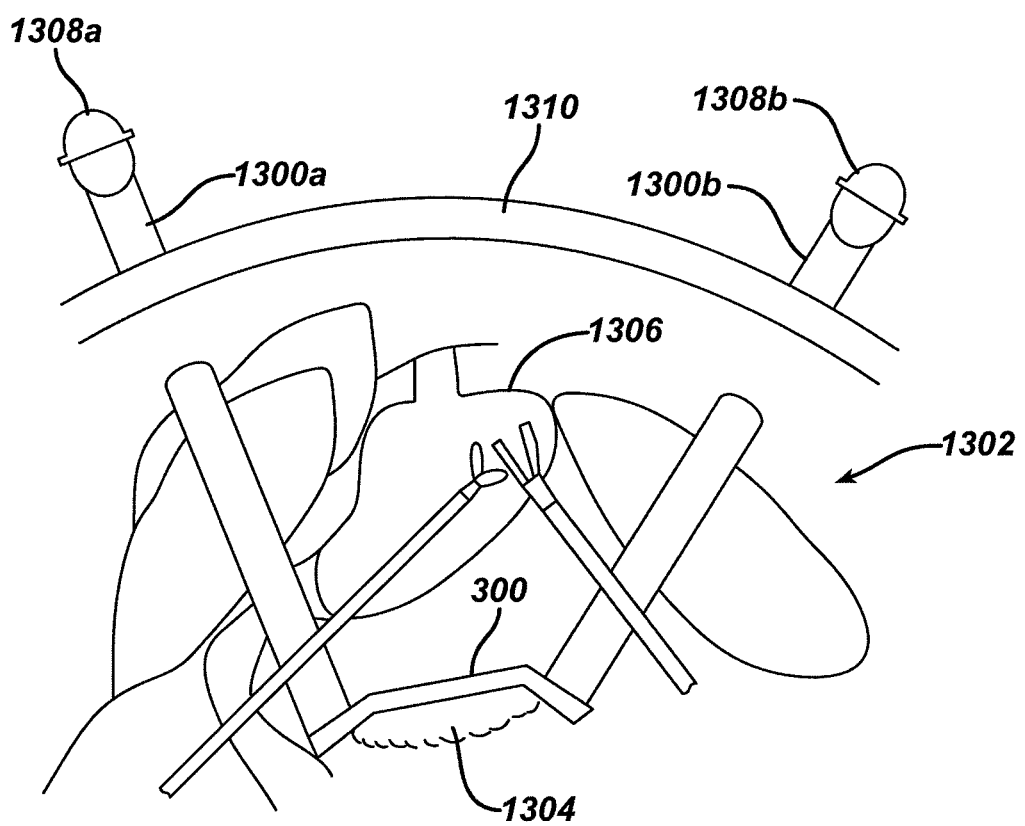
FIG. 13 is a perspective view of the retractor of FIG. 3 shown in use positioned within a body cavity.

In another embodiment, rather than or in addition to using tethers to manipulate the fabric, one or more rods or other grasping devices can be used to manipulate the fabric. FIG. 13 illustrates the retractor 300 of FIG. 3 in use, showing two rods 1300a, 1300b seated in the rod seats 314a, 314b coupled to the fabric 302. The rods 1300a-b (e.g., surgically safe metal rods) are typically seated in the rod seats 314a-b after the fabric 302 has been disposed in a body cavity 1302.

Figure 14:
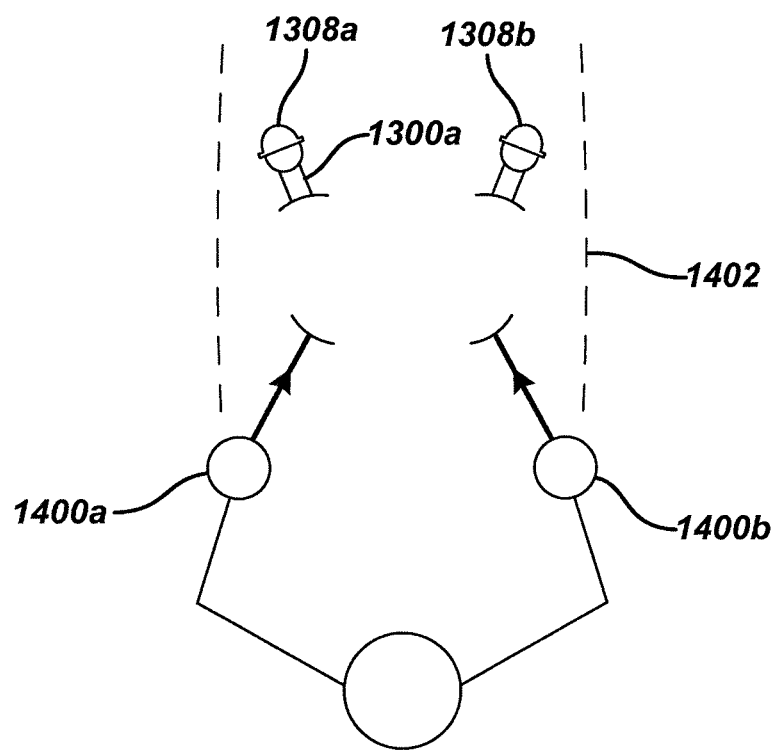
FIG. 14 is a top view showing the surgical system of FIG. 13.

In use, one or both of the rods 1300a-b can be manipulated to move a tissue 1304 away from another tissue 1306 by pulling or pushing one or both of the rods 1300a-b. FIG. 14 illustrates the rods 1300a-b being manipulated by a surgeon's hands 1400a, 1400b outside a body 1402. The rods 1300a-b can one or both be held in a fixed position with a locking mechanism 1308a, 1308b, such as gaskets secured on the rods 1300a-b, outside a body wall 1310. The locking mechanisms 1308a-b in the illustrated embodiment hold the rods 1300a-b in a fixed position, thereby allowing the surgeon to perform a surgical procedure without human manipulation of the rods 1300a-b and thus the fabric 302, unless, for example, the surgeon desires to change the position of the fabric 302 or the held tissue 1304 and uses the rods 1300a-b to do so.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new and/or used instrument(s) is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims.

What is claimed is:

1. A surgical system, comprising:
   a cannula having a proximal end and a distal end;
   a flexible fabric adapted to support tissue, the fabric disposed within the cannula;
   a deployment member permanently coupled to the flexible fabric and adapted to allow the fabric to be pulled through a port, the deployment member being coupled to the flexible fabric at a substantially central midpoint thereof, and the deployment member extending from the distal end of the cannula such that the deployment member can be pulled distally to advance the fabric out of the distal end of the cannula to allow the fabric to support tissue; and
   at least one grasping element coupled to a perimeter of the flexible fabric and adapted to be manipulated to move the flexible fabric and thereby move the tissue, the at least one grasping element extending from the proximal end of the cannula such that the at least one grasping element can be manipulated when the fabric is advanced distally from the cannula to move tissue supported by the fabric.

2. The system of claim 1, wherein the fabric is formed from a mesh material.

3. The system of claim 1, wherein the fabric includes at least one bladder formed therein.

4. The system of claim 3, wherein the at least one bladder is inflatable.

5. The system of claim 1, wherein the at least one grasping element comprises at least one tab having an opening adapted to seat a rod for manipulating the fabric.

6. The system of claim 1, wherein the at least one grasping element comprises at least one tether.

7. The system of claim 1, wherein the fabric includes at least one rib extending along at least a portion thereof and adapted to provide structural integrity to the fabric.

8. The system of claim 7, wherein the at least one rib is formed from a shape memory material.

9. The system of claim 1, wherein the deployment member comprises a ribbon.

10. The system of claim 1, wherein the cannula has a diameter in the range of about 10 mm to 15 mm.

* * * * *